United States Patent
Pfrengle et al.

(10) Patent No.: US 9,788,786 B2
(45) Date of Patent: Oct. 17, 2017

(54) SYSTEMS AND METHODS FOR AUTOMATIC DETECTION AND TESTING OF IMAGES FOR CLINICAL RELEVANCE

(75) Inventors: Udo Pfrengle, Vörstetten (DE); Michael Kohnen, Heitersheim (DE); Arno Blau, Gundelfingen (DE); Thomas Epting, Freiburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 214 days.

(21) Appl. No.: 14/112,369

(22) PCT Filed: May 4, 2011

(86) PCT No.: PCT/EP2011/057105
§ 371 (c)(1),
(2), (4) Date: Dec. 3, 2013

(87) PCT Pub. No.: WO2012/149964
PCT Pub. Date: Nov. 8, 2012

(65) Prior Publication Data
US 2014/0079303 A1 Mar. 20, 2014

(51) Int. Cl.
*A61B 5/00* (2006.01)
*G06T 7/00* (2017.01)
*G06T 7/254* (2017.01)

(52) U.S. Cl.
CPC .......... *A61B 5/4869* (2013.01); *G06T 7/0012* (2013.01); *G06T 7/254* (2017.01);
(Continued)

(58) Field of Classification Search
CPC ................ G06T 7/0012; G06T 7/0083; G06T 2207/30004; G06T 7/0081;
(Continued)

(56) References Cited

U.S. PATENT DOCUMENTS

| 4,907,156 A | 3/1990 | Doi et al. |
| 5,768,441 A * | 6/1998 | Yoshizawa et al. .......... 382/270 |

(Continued)

FOREIGN PATENT DOCUMENTS

| JP | 2002158923 A | 5/2002 |
| JP | 2004152043 A | 5/2004 |

(Continued)

OTHER PUBLICATIONS

Qian et al. "Object Tracking with Self-updating Tracking Window," published in Intelligence and Security Informatics, pp. 82-93, 2007.*

(Continued)

*Primary Examiner* — Duy M Dang
(74) *Attorney, Agent, or Firm* — Lerner, David, Littenberg, Krumholz & Mentlik, LLP

(57) ABSTRACT

Disclosed herein are systems and methods for automatic detection of clinical relevance of images of an anatomical situation. The method includes comparing a first image and a second image and determining whether a difference between the first and second images is at least one of a local type difference and a global type difference. The local type difference is a local difference of the first image and the second image and the global type difference is a global difference between the first image and the second image. The second image is determined as having a clinical relevance if it is determined that the difference between the first image and the second image comprises a local type difference.

27 Claims, 6 Drawing Sheets

(52) U.S. Cl.
CPC ............... *G06T 2207/20004* (2013.01); *G06T 2207/20021* (2013.01); *G06T 2207/20224* (2013.01)

(58) Field of Classification Search
CPC ......... G06T 2207/10081; G06T 11/006; G06T 2207/10116; G06T 5/40; G06T 2207/30068; A61B 6/032; G06F 19/321
See application file for complete search history.

(56) References Cited

U.S. PATENT DOCUMENTS

| | | | | |
|---|---|---|---|---|
| 5,832,055 | A * | 11/1998 | Dewaele | G06T 5/005 250/587 |
| 6,104,831 | A * | 8/2000 | Ruland | G06K 9/00771 348/152 |
| 6,130,707 | A * | 10/2000 | Koller et al. | G08B 13/19602 340/511 |
| 6,148,117 | A * | 11/2000 | Lopez et al. | 382/279 |
| 7,142,600 | B1 * | 11/2006 | Schonfeld et al. | 375/240.16 |
| 7,454,067 | B1 * | 11/2008 | Pati | 382/225 |
| 2002/0090126 | A1 | 7/2002 | Oosawa | |
| 2002/0191850 | A1 * | 12/2002 | Neubauer et al. | 382/206 |
| 2007/0076934 | A1 * | 4/2007 | Krishnan et al. | 382/128 |
| 2008/0205747 | A1 * | 8/2008 | Kuchii | 382/149 |
| 2008/0292194 | A1 * | 11/2008 | Schmidt et al. | 382/217 |
| 2009/0161982 | A1 * | 6/2009 | Tico et al. | 382/275 |
| 2009/0262894 | A1 | 10/2009 | Shukla et al. | |
| 2011/0293190 | A1 * | 12/2011 | O'Callaghan | G06T 7/20 382/197 |
| 2012/0130238 | A1 * | 5/2012 | Muraoka et al. | 600/436 |
| 2013/0050765 | A1 * | 2/2013 | Zhan et al. | 358/3.01 |
| 2013/0243300 | A1 * | 9/2013 | Oda | 382/132 |
| 2015/0016683 | A1 * | 1/2015 | Kinoshita | H04N 5/23219 382/103 |

FOREIGN PATENT DOCUMENTS

| | | |
|---|---|---|
| JP | 2006119891 A | 5/2006 |
| JP | 2008006083 A | 1/2008 |

OTHER PUBLICATIONS

International Search Report and Written Opinion for Application No. PCT/EP2011/057105 dated Jan. 2, 2012.

Radke R J et al: "Image Change Detection Algorithms: A Systematic Survey", IEEE Transactions on Image Processing, IEEE Service Center, Piscataway, NJ, US, vol. 14, No. 3, Mar. 1, 2005, pp. 294-307, XP002602265.

* cited by examiner

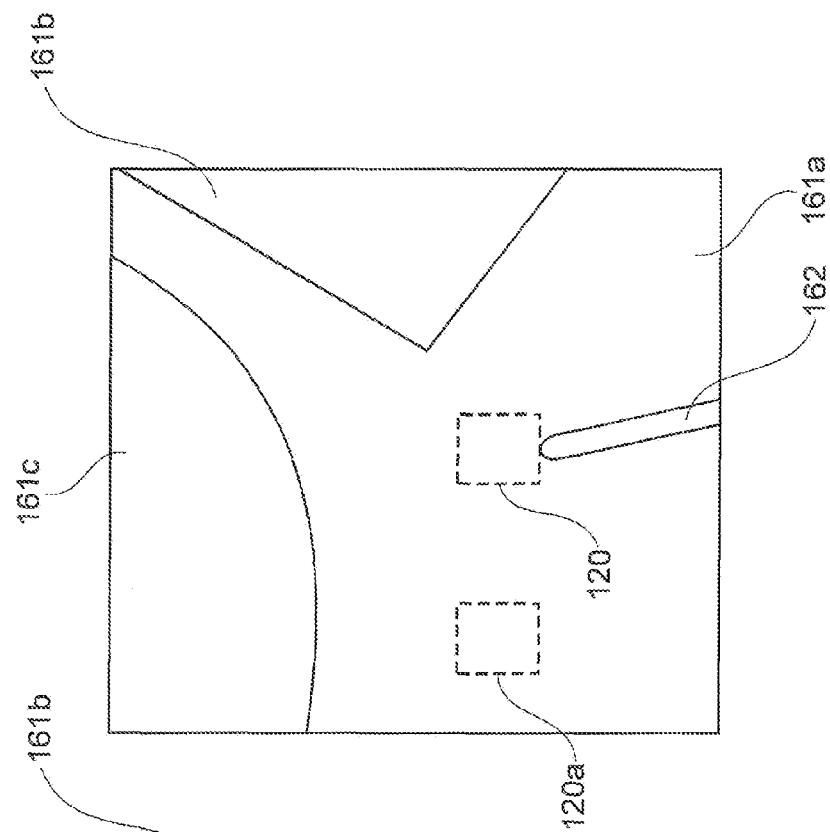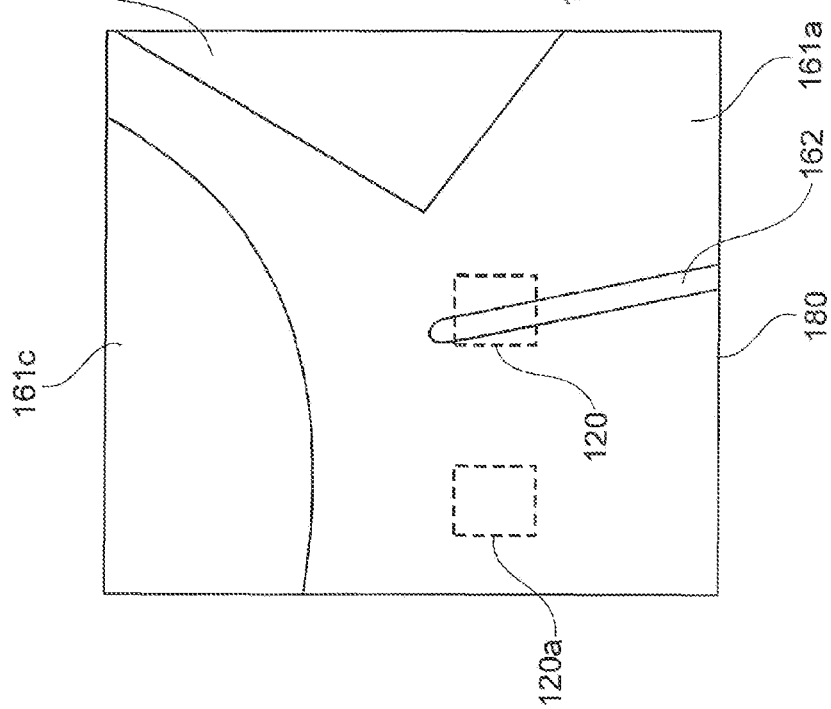

SYSTEMS AND METHODS FOR AUTOMATIC DETECTION AND TESTING OF IMAGES FOR CLINICAL RELEVANCE

CROSS REFERENCE TO RELATED APPLICATIONS

The present application is a national phase entry under 35 U.S.C. §371 of International Application No. PCT/EP2011/057105, filed May 4, 2011, published in English, the entire disclosure of which is hereby incorporated by reference herein.

FIELD OF THE INVENTION

The present invention relates to a method and device as well as a system for automatic detection of clinical relevance of images of an anatomical situation, and in particular to a method and device as well as a system allowing a faster providing of reliable image data.

BACKGROUND OF THE INVENTION

When using image data obtained from an imaging device, such as X-ray, CT, MRT/MRI, for example, for navigation or a computer assisted surgery system, the image date can be provided as a video signal. It is of relevance to detect if there is a new image or not, so that the navigation system or the computer assisted surgery system on demand can use the new content of the new image.

U.S. Pat. Pub. No. 2011/0058026 describes a system and method for detecting a status of an image device. U.S. Pat. Pub. No. 2011/0058026 describes the determination of an intensity of a range of an image outside a mask so that presence of a new image is detected when the newly triggered x-ray device has illuminated the anatomy resulting in a sudden increase in intensity.

SUMMARY OF THE INVENTION

The present invention provides systems and methods for a faster providing of reliable image data.

It should be noted that the following described exemplary embodiments of the invention apply also for a method, a device, a programme element and a computer readable medium.

According to an exemplary embodiment of the invention, a method for automatic detection on clinical relevance of images of an anatomical situation provided by an imaging device comprises taking a first image of the anatomical situation, taking a second image of the anatomical situation, comparing and determining a difference of the first image and the second image, determining whether the difference between the first image and the second image comprises at least one of a local type difference and a global type difference, wherein the local type difference is a local difference of the first image and the second image and wherein the global type difference is a global difference between the first image and the second image, and determining the second image as having a clinical relevance if it is determined that the difference between the first image and the second image comprises a local type difference.

During operation an image having a clinical relevance is an image providing for example the surgeon intra-operatively with new or additional information. In particular, when providing a sequence of images, a subsequent image is considered as having a clinical relevance if it has additional or new information over its mediate or immediate previous image in the sequence. This additional information may be for example an added implant, a modified position of an implant a modified bone or tissue constellation, for example, each over the respective previous image. The method may also include detecting a global type difference before detecting a local type difference. In particular, a clinical relevance may be determined if the global difference exceeds a particular threshold. In case the global difference does not exceed the particular threshold, a local difference type may be detected. If the local difference exceeds a respective threshold, a clinical relevance may be determined. In other words, according to an exemplary embodiment, a clinical relevance may be detected if a global difference exceeds a particular threshold, but in case a global difference does not exceed the particular threshold, a clinical relevance may be detected if a local difference exceeds another particular threshold.

Thus, the device provides the possibility to not only check the presence of a new image, but to also check whether there is a new image content. As navigation systems or computer assisted surgery systems re-calculate the actual status and position of an implant and the respective anatomy, for example, each new image leads to a significant delay before the navigation situation is updated. However, if no new image is provided, no update is required. For this purpose the inventive device compares the content of the images in order to determine the difference. In general a global difference may occur, for example, if a noise is added or removed, a contrast is re-calculated or the like. Such calculation or noise reduction can be carried out by the imaging device like an X-ray C-arm or MRT. Global differences do not mandatorily result from a clinically relevant modification of the image content. The present invention therefore also considers local differences, like changes in a particular image section. If significant changes occur only in a particular location, but not in other locations, this may result in a detection of a clinically relevant modification of the image content. If for example an implant has moved with respect to a bone, all locations remain changed, but the implant location. Thus, from a local difference a clinically relevant modification may be detected.

According to an exemplary embodiment of the invention, the difference of the first image and the second image is determined as difference when exceeding a particular threshold.

Thus, smaller differences like slight noise or minor intensity adoptions can be eliminated, without detecting a significant relevance. Any difference below the threshold will be ignored. Thus, pixel error or the like, for example, will not lead to a detection of a local or global difference.

According to an exemplary embodiment of the invention, comparing and determining a difference of the first image and the second image includes separating each of the first image and the second image into corresponding image blocks each comprising a plurality of pixel and comparing corresponding image blocks.

Thus, the automatic detection can be carried out based on image blocks. These image blocks may include a plurality of pixel, and may be smaller than the entire image. Image blocks allow distinguishing between local and global type differences.

According to an exemplary embodiment of the invention, the local type difference is detected if the difference of the first image and the second image exceeds a first predetermined threshold and wherein the global type difference is detected if the difference of the first image and the second image exceeds a second predetermined threshold, wherein the second threshold is larger than the first threshold.

Thus, the sensitivity of a local type difference detection is higher, as minor differences in a particular location may lead to a detection of a difference being clinically relevant, whereas a global type difference, like changing intensities all over the entire image, will likely not be clinically relevant.

According to an exemplary embodiment of the invention, at least one of the threshold and the first threshold is a locally varying threshold.

Thus, particular constant effects can be eliminated at edges, for example. Further, it can be assumed that the relevant clinical aspect will be identified by image recognition, which may be carried out by a computer assisted surgical system, which aspect may be located at more relevant locations in the image. The image recognition may be carried out based on the first image, so that before considering the second image, relevant image portions can be identified. Such image portions may be a recognized screw tip, K-wire tip etc.

According to an exemplary embodiment of the invention, at least one of the threshold, the first threshold and the second threshold is a dynamic threshold.

Thus, the images can be compared considering dynamic changes. The thresholds can be varied upon detection of specific situations in which it is detected that particular regions include artifacts etc. Further, the threshold can be dynamically adapted based on a ratio of a maximum local difference and a global difference. In other words, if the ratio of a global difference and a maximum local difference exceeds a particular threshold, this may be considered as an indicative for a clinical relevance.

According to an exemplary embodiment of the invention, the method further comprises determining the image block having the maximum local difference and comparing the image block having the maximum local difference with remaining image blocks and determining a local type difference based on the comparison of the image block having the maximum local difference and remaining image blocks.

Thus, it can be determined or confirmed that the maximum difference is a significant difference. In other words, this allows determining whether the difference is a relative large difference, i.e. remaining blocks have a lower difference, or a relative small difference, i.e. the remaining blocks have a similar difference than the maximum difference block.

According to an exemplary embodiment of the invention, the method further comprises determining the image block having a significantly increased local difference and comparing the image block having the significantly increased local difference with image blocks adjacent or in the vicinity of the block with significantly increased local difference and determining a local type difference based on the comparison of the image block having the significantly increased local difference with adjacent image blocks or image blocks in the vicinity of the image block having the significantly increased local difference.

Thus, a gradient of the difference can be determined, so that when having a strong gradient of local differences, i.e. between a block and an adjacent block or vicinity block, the gradient can be used as a measure for the clinical relevance.

According to an exemplary embodiment of the invention, the method further comprises recognizing relevant objects in the first image and determining a local type difference based on a difference of an image block of the first image including the recognized relevant object and a corresponding image block of the second image.

Thus, the relevant portions of the image can be used for determining a local difference and the determination whether or not a clinical relevance has occurred. The relevant portions may be determined based on image information of a computer assisted surgery system which image information had been determined as clinically relevant. This can be carried out by image or object recognition.

According to an exemplary embodiment of the invention, comparing and determining a difference of the first image and the second image includes determining an average and/or a variance of at least a part of corresponding image blocks of the first image and the second image and comparing corresponding image blocks with respect to average and/or variance.

Thus, very simple computing procedures in form of determining an average or mean value or determination of a variance can be applied to obtain an integral value of the entire image block or a plurality of image blocks. Further, a computation intensive one-to-one allocation of pixel can be avoided, as a plurality of pixel in form of an image block together have one or two representing values in form of a mean or average value and a variance.

According to an exemplary embodiment of the invention, a unique size for all image blocks is dynamically adapted based on a detected size of identified objects of the images.

Thus, the image blocks can be adapted to the typical object size. A large number of small objects will possibly lead to a large number of image blocks having a smaller size, and a few large objects will possibly lead to few and large image blocks. The first require more computational capacities than the latter. The detection of the size of relevant objects may be carried out based on image information of a computer assisted surgery system which image information had been determined as clinically relevant.

According to an exemplary embodiment of the invention, comparing and determining a difference of the first image and the second image includes combining a plurality of image blocks to an image block cluster and comparing corresponding image block clusters.

Thus, image blocks can be combined to reduce the number of operations to be conducted for analyzing. The combination of a plurality of image blocks to image block clusters can be conducted dynamically and/or locally distributed.

According to an exemplary embodiment of the invention, a local type difference is determined if at least one of a difference between an image block of the first image and a corresponding image block of the second image and a difference between an image block cluster of the first image and a corresponding image block cluster of the second image exceeds the first threshold.

Thus, the clinically relevant event can be detected and effects resulting in changes below the threshold can be considered as being not relevant. This can be done based on the image blocks as well as the image block clusters.

According to an exemplary embodiment of the invention, the method further comprises detecting a relevant image range, the image range comprising imaged objects, wherein comparing and determining a difference between the first image and the second image is exclusively carried out based on the detected relevant image range.

Thus, the computation can be limited to the relevant image range without useless calculating a black mask being not relevant for the image. In particular any additional written information in the mask area can be ignored, so that a new image will only be provided when detecting changes in the relevant image range.

According to an exemplary embodiment of the invention, the detected relevant image range is used as base for a following image.

Thus, the computation capacity can be reduced as the previous detection serves as a starting base for the present detection.

According to an exemplary embodiment of the invention, the method further comprises detecting a predetermined characteristic of at least one of the first image and second image, wherein the predetermined characteristic is an indicative for at least one of an imaging device type and imaging device manufacturer.

Thus, a manufacturer's logo or signet or type information may be recognized and used for determining the imaging device type or manufacturer. This allows adapting the method to particular characteristics of the device type or the manufacturer. The recognized predetermined characteristic may be for example a characteristic artifact, a logo or trademark, a watermark etc.

According to an exemplary embodiment of the invention, the first image and second image are generated from a permanent video signal output of an imaging device.

Thus, the device can be operated at every imaging apparatus, in particular those having a trigger imaging procedure and triggered image transfer, and those having a permanent image transfer in form of a video signal.

According to an exemplary embodiment of the invention, a device for automatic detection of clinical relevance of images of an anatomical situation provided by an imaging device comprises an image input interface, a first storage for a first image of the anatomical situation taken from the image input interface, a second storage for a second image of the anatomical situation taken from the image input interface, a comparator for comparing and determining a difference between the first image and the second image, a difference type evaluation unit for evaluating the difference type of the first image and the second image, wherein the difference type evaluation unit is adapted for determining at least one of a local type difference and a global type difference, wherein the local type difference is a local difference of the first image and the second image and wherein the global type difference is a global difference between the first image and the second image, and an image selection unit for selecting the second image as having a clinical relevance if it is determined that the difference between the first image and the second image comprises a local type difference.

The effect for the device is analogue to the effect of the method. Thus also the effect of the method as described above will apply for the device.

According to an exemplary embodiment of the invention, the device further comprises a separating unit for separating each of the first image and the second image into image blocks each comprising a plurality of pixels.

According to an exemplary embodiment of the invention, the device further comprises a relevant image range detecting unit for identifying a relevant image range According to an exemplary embodiment of the invention, a system for automatic detection of clinical relevance of images of an anatomical situation provided by an imaging device comprises an imaging device having a permanent video output, a computer assisted surgical system having an image interface for receiving clinically relevant images, an inventive device as described above for automatic detection on clinical relevance of images of an anatomical situation, wherein an image input interface is operatively connected to the permanent video output of the imaging device, and wherein the image interface for receiving clinically relevant images is operatively connected to the image selection unit.

According to an exemplary embodiment of the invention there is provided a computer program element for controlling a device and system for automatic detection on clinical relevance of images of an anatomical situation provided by an imaging device as described above, which, when being executed by a processing unit, is adapted to perform the above described method steps the method for automatic detection on clinical relevance of images of an anatomical situation provided by an imaging device.

According to an exemplary embodiment of the invention there is provided a computer readable medium having stored the above described computer program element.

It should be noted that the above features may also be combined. The combination of the above features may also lead to synergetic effects, even if not explicitly described in detail.

These and other aspects of the present invention will become apparent from and elucidated with reference to the embodiments described hereinafter.

BRIEF DESCRIPTION OF THE DRAWINGS

Exemplary embodiments of the present invention will be described in the following with reference to the following drawings.

DETAILED DESCRIPTION OF EXEMPLARY EMBODIMENTS

A computer assisted surgery system may be operatively connected to an imaging device like an X-ray or the like. Such a computer assisted surgery system may only use detection of a sudden increase of intensity for detecting presence of a new image. Such a system will provide a new image even if the content of the image did not change in a clinically relevant way. This situation may occur when the surgeon again triggers the X-ray device without having modified the anatomical situation. In particular modern imaging devices do not only provide images, but also automatically increase contrast or add text information. For this purpose, the imaging device firstly provides the raw image and after having finished the increased contrast calculation provides the revised image, and later on a further modified image having added text information thereon. However, in the above cases the additional image does not add clinically relevant information to the firstly provided image. The additional image only adds an improved image quality or additional text information or just no significant new image at all in case the surgeon erroneously again triggers the imaging device. In the above mentioned cases a newly provided image, although not having a clinical relevance, will result in a time consuming re-calculation of the navigation, if for example monitoring only the increasing intensity.

Figure 1:
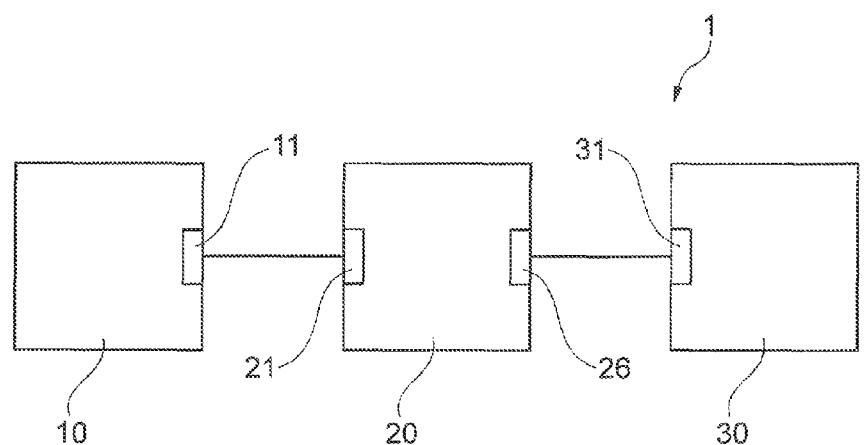
FIG. 1 illustrates the general structure of a system according to an exemplary embodiment of the invention.

FIG. 1 illustrates the general structure of a system according to an exemplary embodiment of the invention. The system 1 comprises an imaging device 10, a device for automatic detection 20, and a computer-assisted surgery system or a navigation system 30. The imaging device 10 comprises a video output interface 11, and the device for automatic detection 20 comprises an image input interface 21. The video output interface 11 and the image input interface 21 are or may be connected to transfer images taken from the imaging device, for example, an X-ray or MRT/MRI device with the device for automatic detection 20. The device for automatic detection will proceed with comparing the images, as will be described later on. The device for automatic detection 20 further comprises an image selecting unit 26, which image selecting unit 26 provides the selected image with the navigation system or computer-assisted surgery system 30, in particular with the image input interface 31 of the navigation system or computer-assisted surgery system 30. Thus, an image will be taken by the imaging device 10, will be transferred to the device for automatic detection, wherein a detection result will be further transmitted as selected image with the navigation system or computer-assisted surgery system 30. The structure of the device for automatic detection 20 will be described in further detail with respect to FIG. 2.

Figure 2:
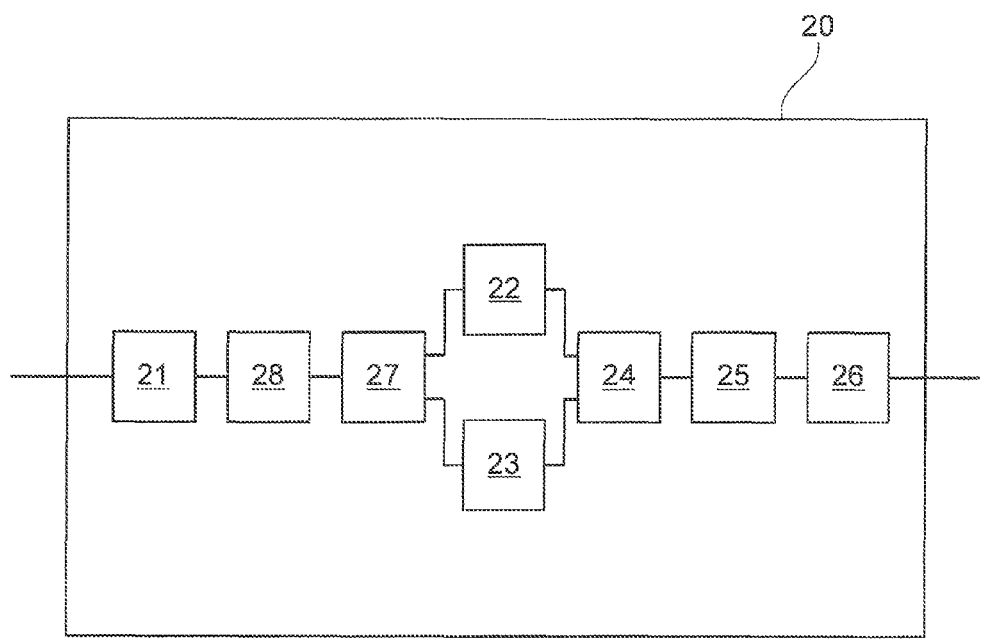
FIG. 2 illustrates the general structure of a device according to an exemplary embodiment of the invention.

FIG. 2 illustrates the general structure of a device for automatic detection according to an exemplary embodiment of the invention. The device for automatic detection 20 comprises an image input interface 21 for receiving images from an imaging device 10, such as an X-ray device, an MRT/MRI device, or a CT device, for example. The device for automatic detection 20 further comprises a unit for determining the relevant image range 28, so that the automatic detection can be carried out based on the relevant image range. Thus, non-relevant image ranges can be left out for the automatic detection, as they possibly do not contain relevant image information. Further, the device for automatic detection 20 may comprise a separating unit 27 for separating the image into image blocks. Thus, the different image blocks can be automatically detected separately, so as to distinguish between a global difference of two images and a local difference between two images, as will be described later on. The device for automatic detection 20 further comprises a first storage for a first image 22 and a second storage for a second image 23. Thus, the images received at the image input interface 21 can be compared by a comparator 24, after being analyzed with respect to a relevant image range by the relevant image range detecting unit 28 and after being separated in different image blocks by the separating unit 27. The result of the comparator will be provided with the difference type evaluation unit 25. After having evaluated the difference type, an image selecting unit 26 will select the respective image to provide the image with the navigation system or computer-assisted surgery system 30. It should be noted that a new image will only be submitted with the computer-assisted surgery system or the navigation system 30 when having detected a surgical relevance. If no surgical relevance is detected, then no image will be provided with the navigation system or computer-assisted surgery system 30. Thus, the computer-assisted surgery system or the navigation system 30 will only conduct a processing of the image in view of the surgical situation if having received an image with a clinical relevance. A clinical relevance may be, for example, a moved implant or a modified position or constellation of an anatomy, so that the respective navigation or assisting information can be updated based on the new image. However, if no clinical relevant information is available, also no update of the navigation or assisting information for the navigation system and the computer-assisted surgery system will be necessary. This procedure will save a lot of computation time, so that the surgeon will only have to wait for a new analysis of the navigation system or computer-assisted surgery system 30 if having received a new image having clinically relevant information.

Figure 3:
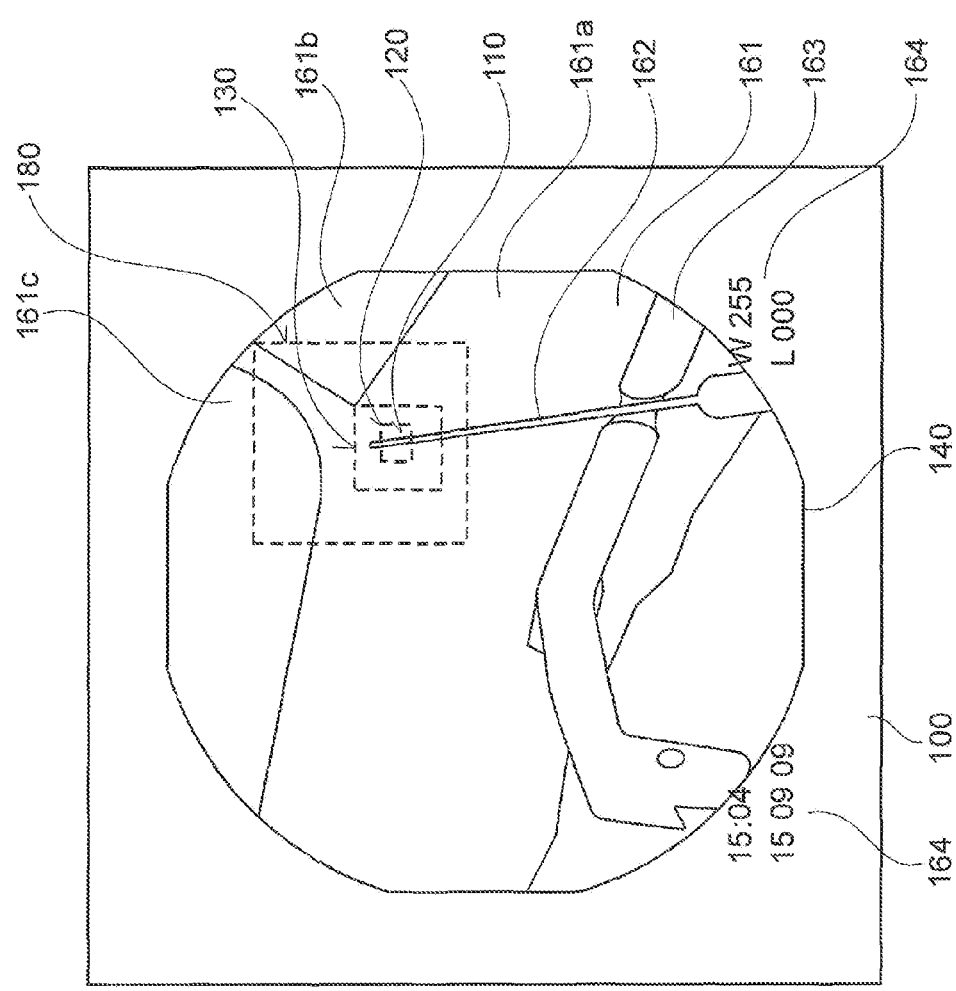
FIG. 3 illustrates the general definitions of the different image details, FIGS. 4A/B illustrate a detailed view of the local type detection.

FIG. 3 illustrates a general definition for the different imaging and image details. FIG. 3 illustrates a sketch with a schematic overview, in which the entire image of an anatomical situation 100 includes a relevant image range 140. The relevant image range 140 includes the image and imaging of the objects as such, wherein the remaining range being included by the image for an anatomical situation, but not included in the relevant imaging range does not comprise an image as such but may comprise for example imaging information, like for example patient data, time and date information or a cursor position or the like, as can be seen from the elements 164. The relevant imaging range 140 illustrates the anatomical situation with the anatomical structure 161, which anatomical structure 161 may include a first anatomical sub-structure 161a, like for example a tissue or a bone, a second anatomical sub-structure 161b, and/or a third anatomical sub-structure 161c. It should be noted that the anatomical sub-structure may also include further implant portions, being already implanted. FIG. 3 further illustrates an implant 163 being already implanted during the operation during which the imaging process takes place, which implant 163 may be for example a gamma nail or the like. Further, FIG. 3 illustrates an additional implant, which may be a temporary implant, like for example a screw, drill, a K-wire or a nail or needle tip 162. In FIG. 3, the relevant range for determining a local difference may be for example the range of the needle or K-wire tip, which needle is moved forward or backward in the anatomical structure. This procedure will be described later on with respect to FIGS. 4A and 4B, which both figures illustrate the enlarged range which is denoted with 180 in FIG. 3. For this description, an image block 120 will be considered for analysis, which image block 120 is close to the needle tip or the K-wire tip. This block 120 may include a plurality of pixels 110, so that the comparison of two images can be carried out based on for example the image block 120. The pixel 110 in FIG. 3 is only schematic and of course much smaller relative to the object 162 as depicted in FIG. 3. A plurality of image blocks 120 can be combined to arrive at an image block cluster 130. In FIG. 3, the image block cluster 130 may include for example nine image blocks 120, three in row and three in a line. It should be noted that the image block cluster may have also more or less imaging blocks, and neither the image block nor the image block cluster have to be in form of a square and may also be in form of a rectangular or any other/free form. Further, the image block cluster may also comprise parts of image blocks, in particular at the edge of the image block cluster.

FIG. 4A and FIG. 4B illustrate the local-type detection in more detail. According to an exemplary embodiment, FIG. 4A may for example illustrate a first image showing the first, the second, and the third anatomical sub-structures 161a, 161b, and 161c. Further, FIG. 4A illustrates the needle 162. As can be seen from FIG. 4A, the needle lies within the image block 120. In a further image, as can be exemplarily seen in FIG. 4B, the needle 162 has been moved, so that the image block 120 does not include the needle any longer. When comparing the image block 120 of FIG. 4A with the image block 120 of FIG. 4B, one can come to the conclusion that the needle 162 is not within the image block 120 any longer and therefore may conclude that this is a clinically relevant situation, as the needle has been moved with respect to the anatomical structure. This analysis between the image block 120 in FIG. 4A and the image block 120 in FIG. 4B can be carried out by calculating an average grey scale value or a mean value of the intensity or colour in the image block 120. In the simplified case shown in FIG. 4A and FIG. 4B the background of the image block 120 is considered as being of white colour and the needle 162 is considered of black colour. The mean value of the greyscale value in the image block 120 in FIG. 4A is almost 30%, assuming that the needle covers 30% of the image block 120. The image block 120 in FIG. 4B, however, does not cover the needle 162 any longer, so that the average grey scale value of the image block 120 is 0%, assuming that the background is white. In real circumstances, of course noise must be expected. When comparing the mean or average value, the result is a significant difference between the mean or average value of the image block 120 in FIG. 4A with respect to the mean value of the image block 120 in FIG. 4B, whereas the difference in the remaining image blocks, e.g. image block 120*a* remains not significant. When exceeding the respective threshold, the device automatically detects that this will be a clinically relevant situation. In particular, this will be determined as a clinically relevant situation, if for example another image block 120*a* in FIG. 4A remains unchanged over the respective image block 120*a* in FIG. 4B. Thus, it can be concluded that the difference between FIG. 4A and FIG. 4B is no global difference, but a local difference in image block 120. In other words, if detecting for example that the grey scale value in image block 120*a* remains at 0%, and the grey scale value of image block 120 changes from 30% to 0%, the detection device may automatically detect a local-type difference as an indicative for a clinically relevant event to be considered by the navigation system or computer-assisted surgical system, if the remaining image blocks remain unchanged. In real circumstances, of course noise must be expected. No clinical relevance may also be detected if the difference over all image blocks is significant but constant for all image blocks. However, if the difference over all blocks is significant, and the difference for only one or a limited number of blocks exceeds the significant difference of the remaining image blocks, a clinical relevance can be determined. The latter example shows that it may be useful applying a dynamic threshold.

In the following, the procedure of automatic detection and testing on clinical relevance of X-ray images provided by imaging device will be exemplarily described in detail. It should be noted that some steps may be left out and some further steps may be added.

The exemplary procedure starts with a periodic digitalization of an analogue video signal with (configurable) sampling frequency. Based on the digitized video signal detection of an e.g. elliptic image area (beam cone) may be carried out. Other distortions like S-form distortions or pincushion distortions can be eliminated by down sampling. The possibility to use an elliptic area makes it possible to also process slightly distorted video images. This allows conduction the whole processing on the original projection without the need for un-distortion. Thus, the original distorted images may be used, for example. The not relevant areas in the image can be ignored such as those that are located in areas outside of the elliptic image area. A configurable or device dependent seam to the inside or to the outside of the elliptic image may be considered. Then, image differences may be analyzed based on down-sampled original images to reduce the amount of image noise and processing time. This may be conducted by calculating a difference image DI compared to the last image passed-through. The evaluation may be carried out by considering a mean value or variance. For this purpose, a mean value and variance over all pixel intensity values of the difference image can be determined as measure for global image change. Images having large differences, i.e. exceeding a large threshold, will be classified as new images and passed through for further processing. The difference image may be separated into overlapping or non-overlapping image blocks of a certain size. It should be noted that the block size may by dynamically varied, e.g. by adapting the block size to the size of typical objects in the image. The process may go on with the calculation of mean value and variance of the pixel intensity values of all blocks together with identification of the block showing a maximum in pixel change. The location of that block having a maximum change may be used in following image processing algorithms. It should be noted that also a block with a second or third etc. strongest change can be considered for processing. This algorithm may include a detection of edges in the image and the calculation of a measure to describe the distribution of image changes to classify the changes as being local or global. This measure may quantify the relation between global changes to local changes and enables to classify the changes accordingly. The algorithm may have implemented a routine for ignoring small global changes which may come from analogue noise or from image processing inside the image source device. The algorithm may also calculate the elliptic area of interest on images which are passed through for further image processing to be used for future images. For this the procedure may guess a circle which roughly covers the inside area based on an even more down-sampled original image. The guessing may use a Hough transform for circles to reduce the search area for the following step and to reduce the effects of image distortion. Further, the procedure may search for bright-to-dark transitions along radial search rays based on the guessed circle, and may use those as candidates for the perimeter of elliptic image area. An additional border area can be left out from considering the image content, as this border area may include written information, as can be seen in FIG. 6*b*, 164, which written information or other disturbing information may extend into the image region. Afterwards, the procedure may repeatedly fit a mathematic model of an ellipse to subsets of candidate points with rejecting outlier points which do not fit well to the ellipse, e.g. using a RANSAC algorithm. The ellipse providing the best fit to the candidate points is the result of the beam cone detection algorithm. The procedure may carry out an automatic detection of an image content specific to the manufacturer and/or imaging device and adjust image processing parameters accordingly. The automatically derived device type may be used as information for optimization of following image processing steps.

The time shift between the both images to be compared may exemplarily be 500 ms. The resolution of the images may be in the field of 500 pixel horizontally and 500 pixel vertically (or 250 horizontally and 250 vertically). The format may be PAL or NTSC or the like. The image blocks may be for example 4 pixel horizontally and 4 pixel vertically.

Figure 5A:
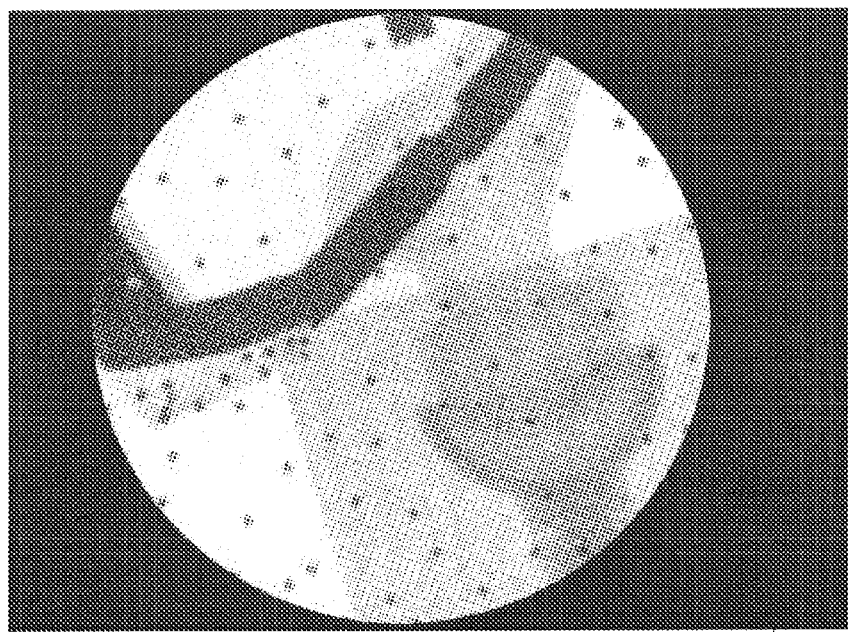
FIGS. 5 A/B illustrate two images that do not have a clinical relevance.
Figure 5B:
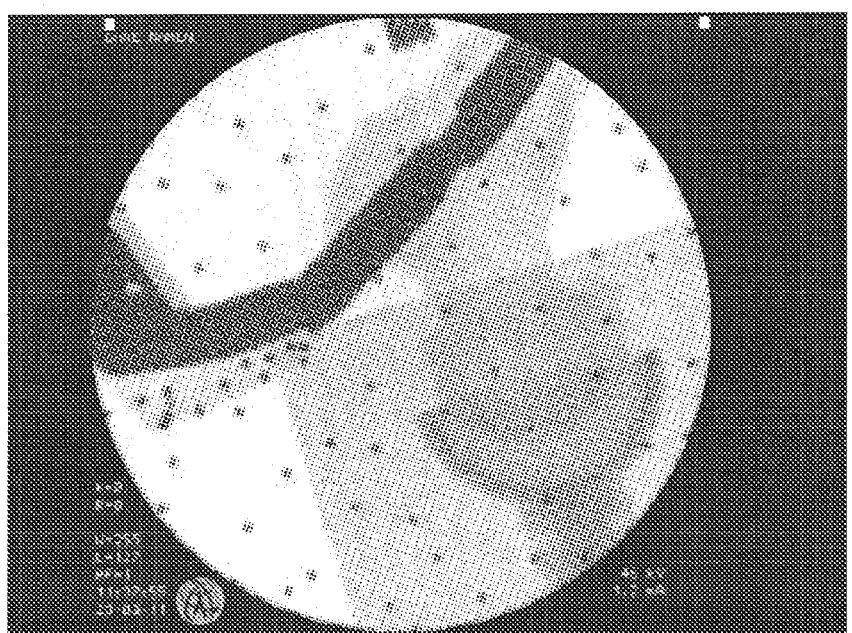

FIG. 5A and FIG. 5B illustrate two images, wherein the difference thereof does not have a clinical relevance. The difference between FIG. 5A and FIG. 5B may be for example a slight change in intensity, which, however, will be the same for each of the image blocks or image clusters, which are not shown in detail in FIGS. 5A and 5B. The difference between FIG. 5A as a first image and FIG. 5B as a second image may be for example an increased contrast, clarified edges or reduced noise or the like which can be carried out by an X-ray device to improve the image quality without taking a new image but based on the first image. In addition, additional image information may be added in a mask area, which is the not-relevant image range outside the disc and inside the entire image 100. This may be for example detailed written information 164, being added after having computed an image with an improved image quality, which improved image, however, does not include a significant clinically relevant event over the first image of FIG. 5A. The additional information 164 may be a time or date information, patient information or any other assisting information for the surgeon.

Figure 6A:
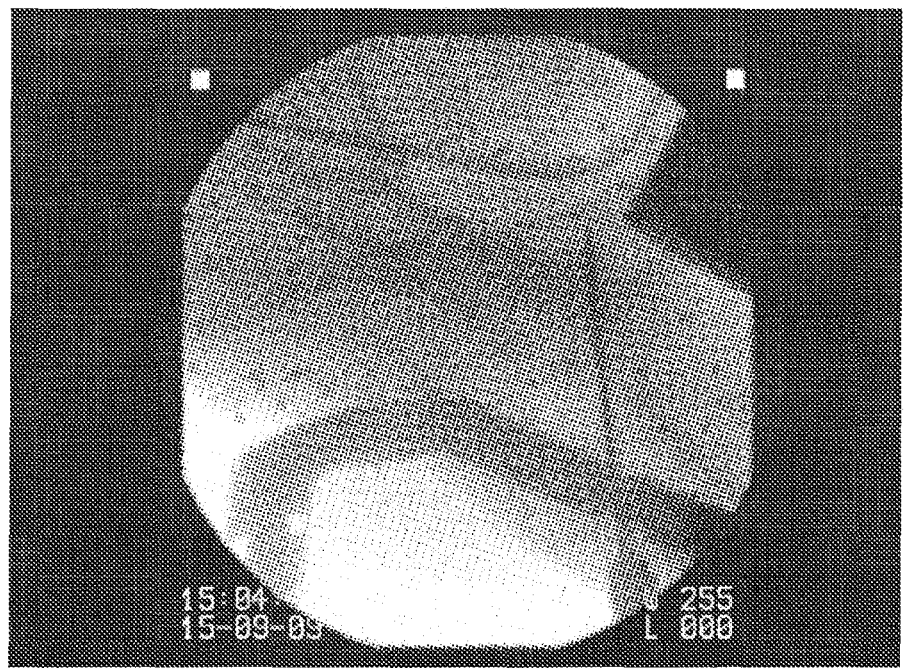
FIGS. 6 A/B illustrates two images that have a clinical relevance.
Figure 6B:
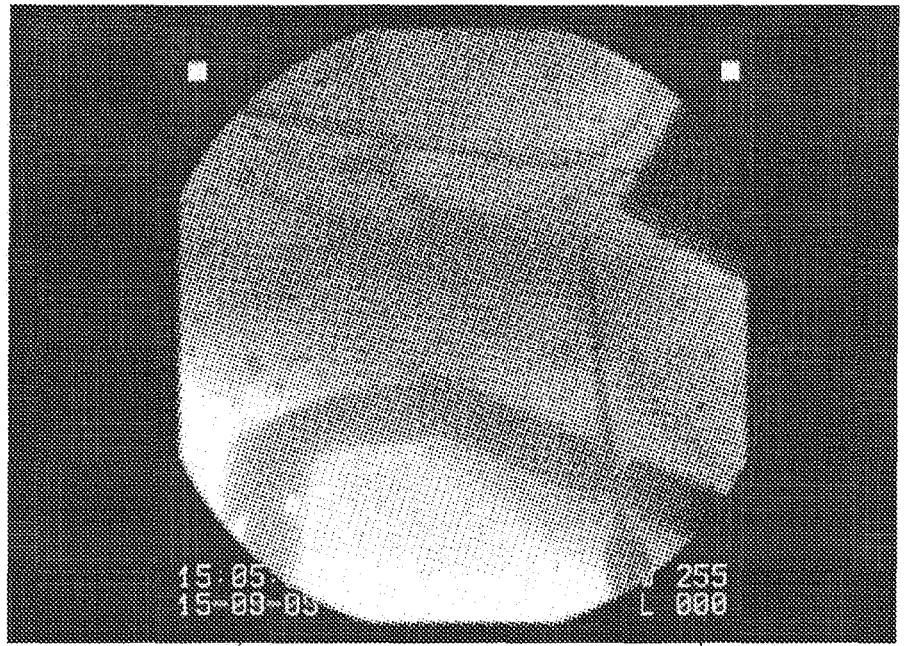

FIG. 6A and FIG. 6B illustrate two images, the difference of which has a clinical relevance. FIG. 3 is the corresponding sketch of FIG. 6A. As illustrated in more detail with respect to FIGS. 3, 4A, and 4B, the difference between FIG. 6A as first image and FIG. 6B as second image is a needle or K-wire movement. Even if detecting a global difference, like for example a changed intensity, clarified edges, added information 164 outside the relevant range 140, the device will further detect an additional local difference, as already described with respect to FIGS. 3, 4A, and 4B. Thus, the device for automatic detection will identify a new image as shown in FIG. 6B, for example, as being of clinical relevance and will provide thereof with the navigation system or the computer-assisted surgery system 30 after selecting this image.

Figure 7:
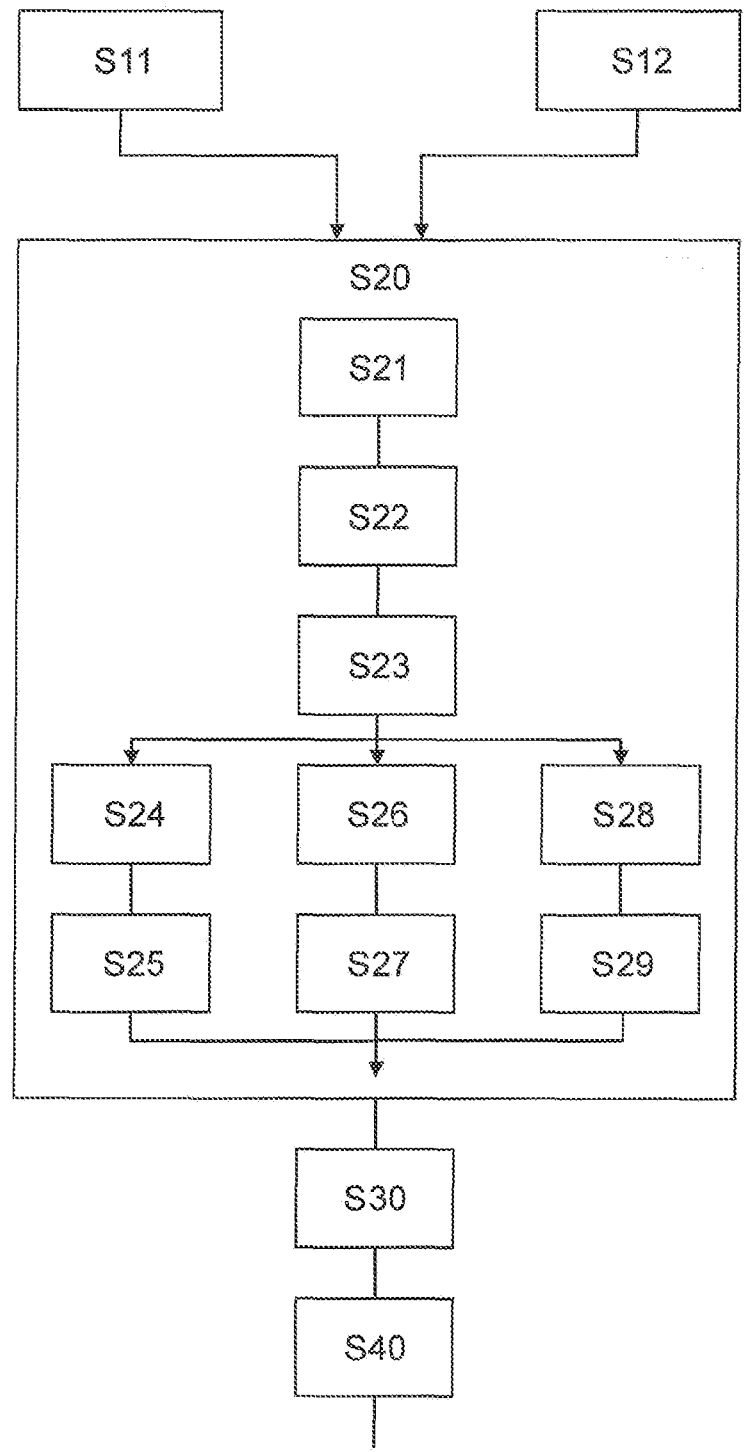
FIG. 7 illustrates an exemplary flow chart of a method according to an exemplary embodiment of the invention.

FIG. 7 illustrates an exemplary flowchart of a method according to an exemplary embodiment of the invention. At first, a first image will be provided in step S11 and a second image will be provided in a step S12. Both images are detected and for example taken from a continuous video stream at a video output interface of the imaging device. Both images will be compared in step S20, wherein the result of the comparison may serve as a basis for determining the presence of a local-type difference and a global-type difference in step S30. Evaluating the local-type difference and the global-type difference, for example when considering a first and a second threshold, allows determining a clinical relevance of the respective image in step S40. The comparison procedure in detail may include detecting a relevant image range in step S21 so that only a relevant image range will be considered for comparison and determining the clinical relevance. Further, a separating into image blocks can take place in step S22 in order to compare respective image blocks. It should be noted that the size of the image blocks may dynamically be adapted in step S23, when considering the typical object size in the image in order to adapt the effort for computation. For example if having only large objects in the image, also the size of the image blocks can be increased so that a very fast procedure can be conducted. After having possibly adapted the size of the blocks, in step S24, the average or mean of the respective image blocks can be determined wherein in the subsequent step S25, the average or mean values can be compared. In the same manner, also the variances can be determined in step S26, wherein in step S27 the variances can be compared. It should be noted that a plurality of image blocks can be combined to form an image block cluster in step S28, wherein in the subsequent step, the image block clusters can be compared in step S29. It should be noted that in step S29, also the several sub-steps in analogy to steps S24 to S27 can be included, as comparing image block clusters may also include determining the average or mean value determination in step S24, comparing of the average or mean value in step S25, determining the variance in step S26, and comparing the variances in step S27. It should be noted that the comparing procedure can be conducted in parallel for image blocks and also image block clusters, for example to compute more relevant ranges with greater detail for image blocks and ranges with lower detail in image block clusters in parallel.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

A computer program may be stored and/or distributed on a suitable medium, such as an optical storage medium or a solid state medium supplied together with or as part of other hardware, but may also be distributed in other forms, such as via the internet or other wired or wireless telecommunication systems.

Although the invention herein has been described with reference to particular embodiments, it is to be understood that theses embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for automatic detection on clinical relevance of images of an anatomical situation provided by an imaging device, the method comprising:
    taking a first image of the anatomical situation at a first time;
    taking a second image of the anatomical situation at a second later time;
    comparing the first image and the second image and determining a difference between the first image and the second image by separating each of the first image and the second image into a plurality of corresponding image blocks each comprising a plurality of pixels, and comparing at least one of the corresponding image blocks of the first and second image;
    determining whether the difference between the first image and the second image comprises at least one of a local type difference and a global type difference, wherein the local type difference is a local difference of the first image and the second image and wherein the global type difference is a global difference between the first image and the second image, and
    determining whether the second image has clinical relevance by determining whether the difference between the first image and the second image comprises a local type difference,
    wherein the local type difference is detected if a first difference of a single image block of the first image and a corresponding single image block of the second image exceeds a first predetermined threshold and wherein the global type difference is detected if a second difference of all of the blocks of the plurality of blocks of the first image and all the blocks of the second image exceeds a second predetermined threshold, wherein the second threshold is larger than the first threshold.

2. The method according to claim 1, wherein the first and second differences are calculated using the same metric.

3. The method according to claim 2, wherein at least one of the threshold and the first threshold is a locally varying threshold.

4. The method according to claim 2, wherein at least one of the threshold, the first threshold and the second threshold is a dynamic threshold.

5. The method according to claim 1, further comprising determining the image block having the maximum local difference and comparing the image block having the maximum local difference with remaining image blocks and determining a local type difference based on the comparison of the image block having the maximum local difference and remaining image blocks.

6. The method according to claim 1, further comprising determining the image block having a significantly increased local difference and comparing the image block having the significantly increased local difference with image blocks in the vicinity of the image block having a significantly increased local difference and determining a local type difference based on the comparison of the image block having the significantly increased local difference with image blocks in the vicinity of the image block having a significantly increased local difference.

7. The method according to claim 1, further comprising recognizing relevant objects in the first image and determining a local type difference based on a difference of an image block of the first image including the recognized relevant object and a corresponding image block of the second image.

8. The method according to claim 1, wherein comparing and determining a difference of the first image and the second image includes determining an average and a variance of at least a part of corresponding image blocks of the first image and the second image and comparing corresponding image blocks with respect to average and variance.

9. The method according to claim 1, wherein a unique size for all image blocks is dynamically adapted based on a detected size of identified objects of the images.

10. The method according to claim 1, wherein comparing and determining a difference of the first image and the second image includes combining a plurality of image blocks to an image block cluster and comparing corresponding image block clusters.

11. The method according to claim 10, wherein the local type difference is determined if at least one of a difference between the image block of the first image and the corresponding image block of the second image and a difference between an image block cluster of the first image and a corresponding image block cluster of the second image exceeds the first threshold.

12. The method according to claim 1, further comprising detecting a relevant image range, the image range comprising imaged objects, wherein comparing and determining a difference between the first image and the second image is exclusively carried out based on the detected relevant image range.

13. The method according to claim 12, wherein the detected relevant image range is used as base for a following image.

14. The method according to claim 1, further comprising detecting a predetermined characteristic of at least one of the first image and second image, wherein the predetermined characteristic is an indicative for at least one of an imaging device type and imaging device manufacturer.

15. The method according to claim 1, wherein the first image and the second image are generated from a permanent video signal output of an imaging device.

16. The method as claimed in claim 1 wherein the size of the image blocks may be dynamically varied based on the size of objects in the image.

17. The method according to claim 1, further comprising recognizing relevant objects inside a relevant image range of the first image and determining a local type difference based on a difference of an image block of the first image including the recognized relevant object and a corresponding image block of the second image.

18. A device for automatic detection on clinical relevance of images of an anatomical situation provided by an imaging device, the device comprising:
an image input interface;
a first storage unit for a first digital x-ray image taken at a first time of the anatomical situation taken from the image input interface;
a second storage unit for a second digital x-ray image taken at a second later time of the anatomical situation taken from the image input interface;
a comparator unit for comparing and determining a difference between the first image and the second image, the comparator unit separating each of the first image and the second image into corresponding image blocks each comprising a plurality of pixels, and comparing at least one of the corresponding image blocks of the first and second image;
a difference type evaluation unit for evaluating the difference type of the first image and the second image, wherein the difference type evaluation unit is adapted for determining at least one of a local type difference and a global type difference, wherein the local type difference is a local difference of the first image and the second image and wherein the global type difference is a global difference between the first image and the second image, and wherein the local type difference is detected if a first difference of an image block of the first image and a corresponding image block of the second image exceeds a first predetermined threshold and wherein the global type difference is detected if a second difference of the first image and the second image exceeds a second predetermined threshold, wherein the second threshold is larger than the first threshold; and
an image selection unit for selecting the second image as having a clinical relevance if it is determined that the difference between the first image and the second image comprises a local type difference.

19. The device according to claim 18, further comprising a separating unit for separating each of the first image and the second image into the corresponding image blocks each comprising a plurality of pixels.

20. The device according to claim 18, further comprising a relevant image range detecting unit for identifying a relevant image range.

21. A system for automatic detection on clinical relevance of images of an anatomical situation provided by an imaging device, the system comprising:
an imaging device having a permanent video output;
a computer assisted surgical system having an image interface for receiving clinically relevant images; and
a device for automatic detection of clinical relevance of images of an anatomical situation provided by an imaging device, the device comprising:
an image input interface;
a first storage unit for a first digital x-ray image taken at a first time of the anatomical situation taken from the image input interface;
a second storage unit for a second digital x-ray image taken at a second later time of the anatomical situation taken from the image input interface;
a comparator unit for comparing and determining a difference between the first image and the second image, the comparator unit separating each of the first image and the second image into corresponding image blocks each comprising a plurality of pixels, and comparing at least one of the corresponding image blocks of the first and second image;
a difference type evaluation unit for evaluating the difference type of the first image and the second image, wherein the difference type evaluation unit is adapted for determining at least one of a local type difference and a global type difference, wherein the local type difference is detected if a first difference of an image block of the first image and a corresponding image block of the second image exceeds a first predetermined threshold and wherein the global type difference is detected if a second difference of the first image and the second image exceeds a second predetermined threshold, wherein the second threshold is larger than the first threshold; and
an image selection unit for selecting the second image as having a clinical relevance if it is determined that the difference between the first image and the second image comprises a local type difference,
wherein the image input interface is operatively connected to the permanent video output of the imaging device, and
wherein the image interface for receiving clinically relevant images is operatively connected to the image selection unit.

22. The system of claim 21, wherein the local type difference is a local difference of the first image and the second image.

23. The system of claim 22, wherein the global type difference is a global difference between the first image and the second image.

24. A method for automatic detection on clinical relevance of images of an anatomical situation provided by an imaging device, the method comprising:
taking a first digital x-ray image of the anatomical situation at a first time;
taking a second digital x-ray image of the anatomical situation at a second later time;
comparing the first image and the second image and determining a difference between the first image and the second image by separating each of the first image and the second image into a plurality of corresponding image blocks each comprising a plurality of pixels, and comparing at least one of the corresponding image blocks of the first and second image;
determining whether the difference between the first image and the second image comprises at least one of a local type difference and a global type difference, wherein the local type difference is a local difference of the first image and the second image and wherein the global type difference is a global difference between the first image and the second image, and determining whether the second image has clinical relevance by determining whether the difference between the first image and the second image comprises a local type difference, wherein the local type difference is detected if a first difference of an image block of the first image and a corresponding image block of the second image exceeds a first predetermined threshold and wherein the global type difference is detected if a second difference of the first image and the second image exceeds a second predetermined threshold, wherein the second threshold is larger than the first threshold.

25. The method according to claim 24, further comprising determining the image block having a significantly increased local difference and comparing the image block having the significantly increased local difference with image blocks in the vicinity of the image block having a significantly increased local difference and determining a local type difference based on the comparison of the image block having the significantly increased local difference with image blocks in the vicinity of the image block having a significantly increased local difference.

26. The method according to claim 24, further comprising recognizing relevant objects in the first image and determining a local type difference based on a difference of an image block of the first image including the recognized relevant object and a corresponding image block of the second image.

27. The method according to claim 24, wherein a unique size for all image blocks is dynamically adapted based on a detected size of identified objects of the images.

* * * * *